(12) United States Patent
Paparatto et al.

(10) Patent No.: US 7,442,817 B1
(45) Date of Patent: Oct. 28, 2008

(54) PROCESS FOR THE PREPARATION OF OLEFIN OXIDES

(75) Inventors: Giuseppe Paparatto, Cinisello Balsamo (IT); Anna Forlin, Vigonza (IT); Paolo Tegon, Oriago (IT)

(73) Assignee: Enichem S.p.A, Milan (IT)

( * ) Notice: Subject to any disclaimer, the term of this patent is extended or adjusted under 35 U.S.C. 154(b) by 0 days.

(21) Appl. No.: 09/627,306

(22) Filed: Jul. 27, 2000

(30) Foreign Application Priority Data

Jul. 27, 1999 (IT) .............................. MI99A1657

(51) Int. Cl.
*C07D 301/12* (2006.01)
(52) U.S. Cl. ..................................... 549/531
(58) Field of Classification Search ................... 549/531
See application file for complete search history.

(56) References Cited

U.S. PATENT DOCUMENTS 6,037,484 A * 3/2000 Grey .......................... 546/531

FOREIGN PATENT DOCUMENTS

| | | |
|---|---|---|
| EP | 0 230 949 | 8/1987 |
| EP | 0 757 043 | 2/1997 |
| EP | 0 940 393 | 9/1999 |
| JP | 11-309378 | * 11/1999 |
| WO | WO 00/17178 | 3/2000 |

OTHER PUBLICATIONS

Derwent Publications, AN 2000-075359, JP 11 309378, Nov. 9, 1999.

* cited by examiner

*Primary Examiner*—Ba Trinh

(57) ABSTRACT

A process in continuous is described for the preparation of oxides of olefins by the direct epoxidation of an olefin with hydrogen peroxide, or compounds capable of producing hydrogen peroxide under the reaction conditions, in a solvent medium, in the presence of a catalytic system consisting of a zeolite containing titanium and a nitrogenated organic base having formula (I).

The process allows the production of high conversions and selectivities of the olefin into the corresponding oxide with a stable catalytic activity over a period of time.

24 Claims, No Drawings

PROCESS FOR THE PREPARATION OF OLEFIN OXIDES

The present invention relates to a process in continuous for the preparation of olefin oxides.

More specifically, the present invention relates to a process in continuous for the preparation of propylene oxide by the direct epoxidation of propylene with hydrogen peroxide, or compounds capable of producing hydrogen peroxide under the reaction conditions, in a solvent medium, in the presence of a catalytic system consisting of a zeolite containing titanium and a nitrogenated organic base having formula (I).

Epoxides, or olefin oxides, are intermediates useful for the preparation of a wide variety of compounds. For example epoxides can be used for the production of glycols, condensation polymers such as polyesters, or for the preparation of intermediates useful in the synthesis of polyurethane foams, elastomers, seals and similar products.

It is known in literature that zeolitic compounds with an MFI structure containing titanium atoms (TS-1) are used as catalysts in the direct epoxidation reactions of olefin compounds with hydrogen peroxide (EP-100119).

However, the acidity which characterizes these catalysts, even if modest, is sufficient to catalyze consecutive solvolytic reactions on the epoxide with the opening of the ring. This leads to an increase in production costs for both the decrease in yield to epoxide and for the separation of the by-products formed.

To overcome these disadvantages, processes have been proposed in the art for improving the catalytic performances of these zeolitic compounds by appropriate activation treatment.

For example, the patent U.S. Pat. No. 4,937,216 describes a process for the preparation of epoxides from olefins and hydrogen peroxide which uses, as catalyst, a titanium silicalite treated, before or during the epoxidation reaction, with a neutralizing agent selected from organic derivatives of silicon of the type X—Si(R)$_3$ or hydrosoluble substances deriving from cations of group I and II with a different base strength.

The patent EP-712.852 discloses an epoxidation process of olefins in the presence of titanium-silicalite which uses as neutralizing agent a non base salt selected from lithium chloride, sodium nitrate, potassium sulfate and ammonium phosphate.

The patent U.S. Pat. No. 5,675,026 describes an epoxidation process which uses as catalyst a titanium-silicalite treated, before or during the reaction, with a neutral salt or acid, selected from $Na_2SO_4$, $(NH_4)_2SO_4$, $NH_4NO_3$ or $NaH_2PO_4$.

Operating according to these known processes, propylene oxide is obtained with a good yield and selectivity.

These processes however have disadvantages deriving from the fact that these catalytic systems have a short duration of the catalytic cycle and consequently require frequent regeneration.

This creates considerable problems from both a technical and economic point of view, above all when the epoxidation process is carried out in continuous.

In fact, a lowering in the production yield of the epoxide and a reduction of the catalytic activity have been observed during the subsequent regeneration phases.

There is therefore the obvious necessity of developing epoxidation processes which allow a high conversion and selectivity to be obtained, simultaneously maintaining the stability of the catalytic activity during the reaction.

It has now been found that these requirements can be satisfied if the epoxidation reaction of olefins is carried out in the presence of suitable nitrogenated bases.

In accordance with this, the present invention relates to a process in continuous for the preparation of olefin oxides by the direct oxidation of an olefin with hydrogen peroxide, or compounds capable of producing hydrogen peroxide under the reaction conditions, in a solvent medium, in the presence of a catalytic system consisting of a synthetic zeolite containing titanium atoms and a nitrogenated base having general formula (I)

wherein: R, $R_1$ and $R_2$, the same or different, can be H, an alkyl group with $C_1$-$C_{10}$ carbon atoms, a —$COR_3$ group wherein $R_3$ is an alkyl group with $C_1$-$C_{10}$ carbon atoms, or a

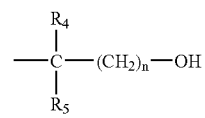

group wherein n is a number ranging from 1 to 10 and $R_4$ and $R_5$ are H or an alkyl group with $C_1$-$C_{10}$ carbon atoms, on the condition that R, $R_1$ and $R_2$ are not contemporaneously H.

Preferred compounds having formula (I) are: methylamine, ethylamine, n-propylamine, diethylamine, n-butylamine, ethanolamine, diethanolamine, triethanolamine and urea.

The compound having formula (I) is fed in continuous and is present in such a concentration as to neutralize the acidity of the reaction mixture.

The concentration however of this compound (I) generally ranges from 5 to 500 ppm (by weight) with respect to the reaction mixture, preferably from 10 to 100 ppm.

The olefin compounds which can be used in the process of the present invention can be selected from organic compounds having at least one double bond and can be aromatic, aliphatic, alkylaromatic, cyclic, branched or linear. They are preferably olefin hydrocarbons having from 2 to 30 carbon atoms in the molecule and containing at least one double bond.

Examples of olefins suitable for the purposes of the present invention are selected from those having general formula (II)

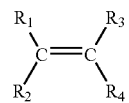

wherein: $R_1$, $R_2$, $R_3$ and $R_4$, the same or different, can be H, an alkyl radical with from 1 to 20 carbon atoms, an aryl radical, an alkylaryl radical with from 7 to 20 carbon atoms, a cycloalkyl radical with from 6 to 10 carbon atoms, an alkylcycloalkyl radical with from 7 to 20 carbon atoms. The radicals $R_1$, $R_2$, $R_3$ and $R_4$, can form, in pairs, saturated or unsaturated rings. These radicals may additionally contain halogen atoms, nitro, nitrile, sulfonic groups and relative esters, carbonyl, hydroxyl, carboxyl, thiol, amine and ether groups.

Examples of olefins which can be epoxidated with the process of the present invention are: ethylene, propylene, allyl chloride, allyl alcohol, butenes, pentenes, hexenes, octeneheptenes-1,1-tridecene, mesityl oxide, isoprene, cyclo-octene, cyclohexene or bicyclic compounds such as norbornenes, pinenes, etc.

The olefins can carry the above substituents both on the unsaturated carbon atoms and on different positions.

The oxidizing agent used in the process of the present invention is hydrogen peroxide ($H_2O_2$) or a compound which is capable of generating $H_2O_2$ under the epoxidation conditions.

An aqueous solution of hydrogen peroxide is preferably used, at a minimum concentration of 1% by weight, preferably with a titer greater than or equal to 35% by weight.

The quantity of hydrogen peroxide with respect to the olefin is not critical, but a molar ratio olefin/$H_2O_2$ ranging from 10:1 to 1:10, preferably from 6:1 to 1:2, is preferably used.

The epoxidation reaction can be carried out in one or more solvents liquid at the epoxidation temperatures. Solvents of a polar nature are typically used, such as alcohols (methanol, ethanol, isopropyl alcohol, t-butyl alcohol, cyclohexanol), ketones (for example acetone, methyl ethyl ketone, acetophenone), ethers (tetrahydrofuran, butyl ether), aliphatic and aromatic hydrocarbons, halogenated hydrocarbons, esters.

Methanol and, among the ketones, acetone, are preferably used. A mixture of methanol/water with a weight ratio ranging from 50/50 to 99/1, is particularly preferred.

The temperatures used in the process of the present invention generally range from 20 to 150° C., preferably from 40 to 100° C. The operating pressures are those which allow the olefin to be maintained in liquid phase at the preset reaction temperature. The operating pressure is generally higher than atmospheric pressure when gaseous olefins are used.

The catalyst which can be used in the process of the present invention is selected from those generally known by the name of titanium-silicalites.

For example titanium-silicalites with an MFI structure can be used, described in the patent U.S. Pat. No. 4,410,501 which also specifies their structural characteristics.

Titanium-silicalites can also be used, in which part of the titanium is substituted by other metals, such as boron, aluminum, iron or gallium. These substituted titanium silicalites and the methods for their preparation are described in European patent applications 226,257, 226,258 and 266,825.

It is also possible to use titanium silicalites with a MEL or intermediate MFI/MEL structure described in Belgian patent 1,001,038. Other titanium-silicalites can be selected from beta zeolites containing titanium and having a BEA structure, described in Spanish patent 2,037,596, ZSM-12 containing titanium and optionally aluminum, described in "Journal of Chemical Communications, 1992, page 745).

The preferred catalyst according to the present invention is titanium-silicalite having the general formula:

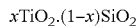

$$xTiO_2 \cdot (1-x)SiO_2$$

wherein: x represents a number ranging from 0.0001 to 0.04, preferably from 0.01 to 0.025, and described, for example, in U.S. Pat. Nos. 4,410,501, 4,824,976, 4,666,692, 4,656,016, 4,859,785, 4,937,216.

The quantity of catalyst used in the process of the present invention is not critical; it is selected however in such a way as to allow the epoxidation reaction to be completed in as short a time as possible.

The quantity of catalyst is generally selected in relation to various parameters, such as the reaction temperature, the reactivity and concentration of the olefins, the concentration of hydrogen peroxide, the type and composition of the solvent, the catalytic activity and type of reactor or reaction system used.

The quantity of catalyst typically ranges from 1 to 15% by weight with respect to the reaction mixture and, preferably, from 4 to 10% by weight.

The catalyst can be used in the form of powder, pellets, microspheres, extruded product or other convenient physical forms.

The epoxidation process of the present invention can be carried out in batch, semi-continuous or, preferably, in continuous.

Various types of reactor can be used in the process of the present invention, for example a slurry reactor or a fixed-bed reactor.

The epoxidation process is preferably carried out in continuous, by feeding into a reaction zone containing the catalyst: the solvent, hydrogen peroxide, the olefin and the compound having general formula (I).

The epoxide obtained with the process of the present invention can be separated and recovered from the reaction mixture using suitable techniques such as fractionated distillation.

The following examples have the sole purpose of describing the present invention in greater detail and should in no way be considered as limiting its scope.

EXAMPLE 1 (COMPARATIVE)

Oxidation of Propylene

The epoxidation reaction is carried out in a stirred, 1.5 liter, AISI 316L steel reactor, equipped with a thermostat-regulation system, level control, pressure control and filter for continuously removing the solution, maintaining the catalyst in the reactor.

760 g of a solution of methanol/water (93/7) and 40 g of titanium silicalite TS-1 (EniChem, with a titanium content equal to 2.05% by weight) are initially charged.

After thermostat-regulating the system at 60° C. and pressurizing with propylene to 12 bar, the following products are fed in continuous by means of pumps:

1. 1970 g/hour of a solution of methanol/water 92.8/7.2 by weight 2. 230 g/hour of an aqueous solution of $H_2O_2$ at 35% by weight 3. propylene 4. 100 g/hour of water.

The overall reaction mixture in the feeding (without propylene) is equal to 2300 g/hour and its composition is the following:

$H_2O_2$ 3.5%, $H_2O$ 17%, MeOH 79.5%.

The pressure in the reactor is maintained at 12 bar, feeding propylene.

The reaction trend is followed by taking samples every two hours and determining the residual $H_2O_2$ by titration with sodium thiosulfate and the reaction products by gaschromatography.

The results are indicated in Table 1.

TABLE 1

| reaction hours | H$_2$O$_2$ conversion % | PO selectivity % |
| --- | --- | --- |
| 6 | 90 | 67 |
| 16 | 82 | 75 |
| 30 | 75 | 80 |

EXAMPLE 2 (COMPARATIVE)

The reaction is carried out under the same conditions described in example 1, but feeding in continuous (100 g/hour) an aqueous solution containing 0.115% by weight of sodium acetate, corresponding to 50 ppm of the reaction mixture. The results are indicated in table 2.

TABLE 2

| Reaction hours | H$_2$O$_2$ conversion % | PO selectivity % |
| --- | --- | --- |
| 6 | 96 | 84 |
| 16 | 94 | 91 |
| 30 | 87 | 96 |

EXAMPLE 3 (COMPARATIVE)

The same procedure is adopted as in example 1, but feeding in continuous (100 g/hour) an aqueous solution containing 0.092% by weight of NaNO$_3$, corresponding to 40 ppm in the reaction mixture. The results are shown in table 3.

TABLE 3

| Reaction hours | H$_2$O$_2$ conversion % | PO selectivity % |
| --- | --- | --- |
| 6 | 92 | 71 |
| 16 | 87 | 82 |
| 30 | 84 | 86 |

EXAMPLE 4 (COMPARATIVE)

The same procedure is adopted as in example 1, but feeding in continuous (100 g/hour) an aqueous solution containing 0.046% by weight of NaOH, corresponding to 20 ppm in the reaction mixture. The results are shown in table 4.

TABLE 4

| Reaction hours | H$_2$O$_2$ conversion % | PO selectivity % |
| --- | --- | --- |
| 6 | 85 | 93 |
| 16 | 65 | 97.5 |
| 30 | 45 | 98 |

EXAMPLE 5

The same procedure is adopted as in example 1, but feeding (100 g/hour) an aqueous solution containing 0.23% of ethanolamine, corresponding to 100 ppm in the reaction mixture. The results are shown in table 5.

TABLE 5

| Reaction hours | H$_2$O$_2$ conversion % | PO selectivity % |
| --- | --- | --- |
| 6 | 94 | 97.5 |
| 30 | 92.5 | 97.2 |
| 40 | 89 | 97.4 |

EXAMPLE 6

The same procedure is adopted as in example 1, but feeding (100 g/hour) an aqueous solution containing 0.23% of ethylamine, corresponding to 100 ppm in the reaction mixture. The results are shown in table 6.

TABLE 6

| Reaction hours | H$_2$O$_2$ conversion % | PO selectivity % |
| --- | --- | --- |
| 6 | 95 | 96.8 |
| 30 | 92 | 96.5 |
| 40 | 91 | 97.5 |

EXAMPLE 7

The same procedure is adopted as in example 1, but feeding (100 g/hour) an aqueous solution containing 0.23% of n-propylamine, corresponding to 100 ppm in the reaction mixture. The results are shown in table 7.

TABLE 7

| Reaction hours | H$_2$O$_2$ conversion % | PO selectivity % |
| --- | --- | --- |
| 6 | 92 | 96.5 |
| 30 | 91.5 | 96.8 |
| 40 | 91.7 | 97 |

The invention claimed is:

1. A process in continuous for the preparation of olefin oxides by the direct epoxidation of an olefin with hydrogen peroxide, or compounds capable of producing hydrogen peroxide under the reaction conditions, in a solvent medium, in the presence of a catalytic system consisting of a zeolite containing titanium atoms and a nitrogenated base having general formula (I)

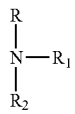

(I)

wherein: R, R$_1$ and R$_2$, the same or different, can be H, an alkyl group with C$_1$-C$_{10}$ carbon atoms, a —COR$_3$ group wherein R$_3$ is an alkyl group with C$_1$-C$_{10}$ carbon atoms, or a

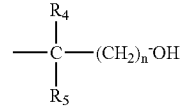

group, wherein n is a number ranging from 1 to 10 and $R_4$ and $R_5$ are H or an alkyl group with $C_1$-$C_{10}$ carbon atoms, on the condition that R, $R_1$ and $R_2$ are not contemporaneously H.

2. The process according to claim 1, wherein the compound having formula (I) is selected from ethylamine, n-propylamine, diethylamine, n-butylamine, ethanolamine, diethanolamine and triethanolamine.

3. The process according to claim 1, wherein the starting olefin compounds are selected from aromatic, aliphatic, alkylaromatic, cyclic, branched or linear organic compounds, having at least one double bond.

4. The process according to claim 3, wherein the olefin compounds are selected from olefin hydrocarbons having from 2 to 30 carbon atoms in the molecule and containing at least one double bond.

5. The process according to claim 4, wherein the olefin compounds are selected from those having general formula (II)

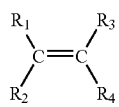

wherein: $R_1$, $R_2$, $R_3$ and $R_4$, the same or different, can be H, an alkyl radical with from 1 to 20 carbon atoms, an aryl radical, an alkylaryl radical with from 7 to 20 carbon atoms, a cycloalkyl radical with from 6 to 10 carbon atoms, an alkylcycloalkyl radical with from 7 to 20 carbon atoms.

6. The process according to claim 5, wherein the radicals $R_1$, $R_2$, $R_3$ and $R_4$ can form, in pairs, saturated or unsaturated rings.

7. The process according to claim 4, wherein the radicals $R_1$, $R_2$, $R_3$ and $R_4$ can contain substituents selected from halogens, nitro, nitrile, sulfonic groups and relative esters, carbonyl, hydroxyl, carboxyl, thio amine and ether groups.

8. The process according to claim 1, wherein the olefin is propylene.

9. The process according to claim 1, wherein the compound having formula (I) is used in a quantity ranging from 5 to 500 ppm by weight with respect to the reaction mixture.

10. The process according to claim 9, wherein the compound having formula (I) is used in a quantity ranging from 10 to 100 ppm by weight with respect to the reaction mixture.

11. The process according to claim 1, wherein the hydrogen peroxide is used as an aqueous solution with a minimum titer of 1% by weight.

12. The process according to claim 11, wherein the hydrogen peroxide is used as an aqueous solution with a titer equal to or higher than 35% by weight.

13. The process according claim 1, wherein the molar ratio between olefin and hydrogen peroxide ranges from 10/1 to 1/10.

14. The process according claim 13, wherein the molar ratio between olefin and hydrogen peroxide ranges from 6/1 to 1/2.

15. The process according to claim 1, wherein the catalyst is selected from titanium silicalites having the following general formula:

$$x\text{TiO}_2.(1-x)\text{SiO}_2$$

wherein: x ranges from 0.0001 to 0.04.

16. The process according to claim 15, wherein the value of x ranges from 0.01 to 0.025.

17. The process according to claim 15, wherein in the titanium silicalite part of the titanium is substituted by metals selected from boron, aluminum, iron or gallium.

18. The process according to claim 1, wherein the epoxidation reaction is carried out in one or more solvents, liquid at the epoxidation temperatures, selected from alcohols, ketones, ethers, aliphatic and aromatic hydrocarbons, halogenated hydrocarbons, esters and glycols.

19. The process according to claim 18, wherein the alcohols are selected from methanol, ethanol, isopropyl alcohol, t-butyl alcohol, cyclohexanol.

20. The process according to claim 18, wherein the ketones are selected from acetone, methyl ethyl ketone, acetophenone.

21. The process according to claim 18, wherein the ethers are selected from tetrahydrofuran and butyl ether.

22. The process according to claim 18, wherein the solvent medium is a mixture of methanol/water with a weight ratio ranging from 50/50 and 99/1.

23. The process according to claim 1, wherein the epoxidation reaction is carried out at a temperature ranging from 20 to 150° C.

24. The process according to claim 21, wherein the temperature ranges from 40 to 100° C.

* * * * *